United States Patent
Heisler et al.

(10) Patent No.: US 10,045,933 B2
(45) Date of Patent: Aug. 14, 2018

(54) QUICK-PENETRATING SOFT SKIN-CARE CREAM

(71) Applicant: DEB IP LIMITED, Denby, Derbyshire (GB)

(72) Inventors: Eckhard Heisler, Geldern (DE); Markus Hemming, Oberhausen (DE); Carina Drewes, Krefeld (DE); Nicole Wans, Krefeld (DE)

(73) Assignee: DEB IP LIMITED, Denby, Derbyshire (GB)

( * ) Notice: Subject to any disclaimer, the term of this patent is extended or adjusted under 35 U.S.C. 154(b) by 208 days.

(21) Appl. No.: 14/426,084

(22) PCT Filed: Aug. 8, 2013

(86) PCT No.: PCT/EP2013/066620
§ 371 (c)(1),
(2) Date: Mar. 4, 2015

(87) PCT Pub. No.: WO2014/037183
PCT Pub. Date: Mar. 13, 2014

(65) Prior Publication Data
US 2015/0231058 A1    Aug. 20, 2015

(30) Foreign Application Priority Data
Sep. 5, 2012 (EP) .................... 12183046

(51) Int. Cl.
| | | |
|---|---|---|
| *A61K 8/92* | (2006.01) | |
| *A61K 8/34* | (2006.01) | |
| *A61K 8/37* | (2006.01) | |
| *A61Q 19/00* | (2006.01) | |
| *A61K 8/44* | (2006.01) | |
| *A61K 8/49* | (2006.01) | |
| *A61K 8/42* | (2006.01) | |
| *A61K 8/81* | (2006.01) | |

(52) U.S. Cl.
CPC .............. *A61K 8/922* (2013.01); *A61K 8/342* (2013.01); *A61K 8/345* (2013.01); *A61K 8/37* (2013.01); *A61K 8/42* (2013.01); *A61K 8/44* (2013.01); *A61K 8/4946* (2013.01); *A61K 8/8147* (2013.01); *A61K 8/8152* (2013.01); *A61Q 19/00* (2013.01); *A61Q 19/007* (2013.01); *A61K 2800/30* (2013.01); *A61K 2800/34* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,194,260 A | * | 3/1993 | Grollier | A61K 8/044 |
| | | | | 424/401 |
| 7,306,810 B1 | * | 12/2007 | Spencer | A61K 8/27 |
| | | | | 424/401 |
| 2004/0228824 A1 | * | 11/2004 | Voigt | A61K 8/062 |
| | | | | 424/70.16 |
| 2005/0142154 A1 | * | 6/2005 | Blatt | A61K 8/44 |
| | | | | 424/401 |
| 2006/0194057 A1 | | 8/2006 | Pfluecker et al. | |
| 2007/0141014 A1 | | 6/2007 | Pflucker et al. | |
| 2007/0248555 A1 | * | 10/2007 | Watson | A61K 8/34 |
| | | | | 424/70.13 |

FOREIGN PATENT DOCUMENTS

| | | |
|---|---|---|
| EP | 1325736 | 7/2003 |
| JP | 1991501127 | 3/1991 |
| JP | 2006528706 | 12/2006 |
| JP | 2007524675 | 8/2007 |
| WO | 8910121 | 11/1989 |
| WO | 03/017952 | 3/2003 |

OTHER PUBLICATIONS

Natural Wellbeing, Allantoin, Jun. 10, 2012, pp. 1-3.*
Tegosoft AC, (Mar. 7, 2012), pp. 1-3.*
Wax, Wikipedia, Apr. 5, 2013, pp. 1-5, XP055062323, Retrieved from the Internet: URL:http://en.wikipedia.org/wiki/Wax [retrieved on May 8, 2013] Abschnitt "Types"; Abbildung rechts oben; p. 1.
International Search Report in corresponding PCT Application No. PCT/EP2013/066620, dated Sep. 9, 2014.

* cited by examiner

*Primary Examiner* — Jennifer A Berrios

(57) ABSTRACT

The invention pertains to the field of cosmetic and/or dermatological compositions and relates to quick-penetrating skin care compositions for topical application to human skin, containing wax components, carbomers, certain fatty alcohols, emollients, certain fatty acid and fatty alcohol esters, and at least one active ingredient selected from among creatine, allantoin, and/or glycerin. The invention further relates to methods for the production and to uses of such compositions.

20 Claims, No Drawings

QUICK-PENETRATING SOFT SKIN-CARE CREAM

CROSS-REFERENCE TO RELATED APPLICATIONS

This application is a National Phase application claiming the benefit of the international PCT Patent Application No. PCT/EP2013/066620, filed on Aug. 8, 2013, in the German language, which claims priority to EP Application No. 12183046.7, filed on Sep. 5, 2012, in the German language, the entire contents of which are incorporated herein by reference.

FIELD

The invention pertains to the field of cosmetic and/or dermatological compositions and relates to quick-penetrating skin care compositions for topical application to human skin, containing wax components, carbomers, certain fatty alcohols, emollients, certain fatty acid and fatty alcohol esters, and at least one active ingredient selected from among creatine, allantoin, and/or glycerin. The invention further relates to methods for the production and to uses of such compositions.

BACKGROUND

With a surface area of about 1.5 to 2.0 $m^2$, the human skin is the human organ with the largest surface area that performs vital functions for the body. For this, the skin contains blood and lymph vessels, through the walls of which the exchange of lymphatic fluid, gases, nutrients and waste materials can take place in order, for example, to ensure nutrition and metabolism. Other functions of the skin are the regulation of body temperature, protecting the body against dehydration and against external mechanical, chemical and bacterial action. In doing so, the secretions of skin glands keep the skin supple and help in regulating the water balance of the skin. In addition, the skin provides the organism, among other things, via free nerve endings, with tactile, heat and cold and pain stimuli and thus has the function of a sensory organ.

The various products offered for hygiene, personal care and cosmetics, such as, for example, skin cleansing, skin protection and skin care products, are therefore not only just for the cleansing, protection and care of the skin, but they also provide a quality of life and ensure the well-being of the person.

As a body shell, the human skin represents the connection with, but at the same time also the delineation of the human body from its external world. In particular, it provides the means of contact with everything that the human organism needs to live—but also what may endanger it.

Therefore, it is especially important to care for the human skin and to protect it from environmental influences. The past history of skin care products can therefore be traced far back into the history of human development itself. As the requirements for skin care products can be very different, the range of different skin care products grew wider over the years in order to adapt better to different needs of consumers and different stresses on the skin in relation to the particular environment. In particular, significantly wider demands have been placed on skin care products for use in the workplace that go far beyond the scope of common household skin care products. According to W. Dicke (see W. Dicke; I. Funk-Stendel, B. Marschner, F. Zuther: "All about skin protection, skin cleansing, skin care", 5th updated and expanded edition (115-118); October 2005) modern skin care products are preparations that contribute to the conservation and restoration of the physiological hydro-lipid emulsion in the upper skin layers. Skin care products often contain special ingredients that support the regeneration process of the skin. Accordingly, products for the care and/or health maintenance of the skin, as well as skin protection products, must be adapted, for example, to the demands of the workplace and to the degree of stress on the skin.

Since endogenous lipids and natural moisturising factors are extracted from the skin by repeated hand washing or working in a humid environment, the supply of moisture in skin care is of central importance. In this context, moisturising factors have the primary task of retaining moisture in the skin and slowing down evaporation of water from the skin. If these components are removed from the skin, there is an increased evaporation of water and the skin gives a dry and greasy impression, which can also be regarded as a precursor to degenerative dermatosis. Therefore, in addition to lipids and moisture, water-binding factors such as lactic acid are often used in skin care products also. If the skin care product is an oil-in-water emulsion, special requirements are placed on the formulation, because it can also lead to a drying of the skin when applying high water content emulsions due to a so-called "wick effect". This must be taken into account in the development of a skin care product by combining different moisturising factors. Finally, with regard to the potential application of a skin protective product, acceptance of the product by the end consumer plays a key role. This means, in particular, that parameters such as absorption ability, the imprint behaviour, the ability to grip after application, oily sheen and the smell are paramount.

Also, in the decision made by an operation for a skin care product to use in the workplace, quite different, additional parameters over and above these play a crucial role. In addition to properties concerning care and protection of the skin against everyday work influences, the behaviour, for example, of the corresponding skin care product after application is crucial. After application of the skin care product, the treated areas of skin, especially the hands and forearms, come into contact inevitably with the working environment. The result of this is that surfaces of any kind at the workplace may be contaminated with unwanted residues from the skin care products through contact with treated areas of skin. This is especially critical if the contact is made with sensitive surfaces, products or production equipment. In the worst case, effects involving, for example, hydrophilic or emulsifying ingredients of skin care products on water-repellent surfaces, act in such a way on the surface in question that changes may be caused, such as in colour, consistency, or the chemical composition of surfaces. In addition, residues on workpieces or intermediate products can have a negative effect on the follow-up product. In addition, the creaming of hands with skin care products can affect the grip and thus make working with tools more dangerous.

There is therefore still a need for skin care products, that, on the one hand, meet the high demands of the consumer in terms of care and protection sufficiently and, on the other hand, correspond to the requirements of businesses by being universally applicable, without excessive consideration for any critical work environment and sensitive surfaces.

SUMMARY

The task of the present invention was therefore to provide compositions for topical application to the skin, ensuring a universal applicability in the work environment, and thus achieving a higher acceptance in daily use in businesses; and which have excellent care properties and have suitable properties with respect to the stability of the composition.

This objective has been achieved by cosmetic and/or dermatological compositions wherein the compositions contain, as a combination of active ingredients, and based on the total weight of the particular composition a) 0.2 to 0.8% by wt. of at least one wax body
b) 0.3 to 1% by wt. of at least one polymer based on at least one acrylic acid monomer and/or at least one ester of an acrylic acid monomer;
c) 0.1 to 0.75% by wt. of at least one linear, saturated, unsubstituted fatty alcohol having 12 to 20 carbon atoms
d) 3 to 6% by wt. of at least one emollient
e) from 0.5 to 1.5% by wt. of at least one linear, saturated, unsubstituted ester having 20 to 34 carbon atoms of a fatty acid and a fatty alcohol, and
f) at least one active ingredient selected from creatine, allantoin and/or glycerin.

It has been shown that combinations of active ingredients resolve the above-mentioned objective very well in the specified weight ranges. It is particularly noteworthy that compositions according to the invention are stable even at an elevated concentration of electrolytes, for example in the presence of salts, such as, among others, sodium and/or potassium salts. Compositions according to the invention exhibit a remarkably good absorption behaviour in the skin and are suitable therefore in businesses in particular, i.e. through daily use for the care and protection of the skin while work is being performed. The rapid absorption behaviour has the positive effect, besides the pleasant, non-sticky sensation of the user/consumer, that contact with surfaces by skin areas treated with compositions according to the invention results in the minimisation of residues on the surfaces in question. This applies to contact with surfaces of any kind, on which the previous use of skin care products can leave undesirable residues. Compositions according to the invention leave especially few residues on water-repellent substrates such as plastic surfaces, such as, amongst other things, keyboards and telephones, electronic components such as printed circuit boards, glass surfaces, plexiglass or modified glass surfaces, surfaces to be painted, lacquers, especially automotive lacquers, varnishes, ceramics, porcelain, metal, alloys, stone, wood and machined wood surfaces, laboratory materials or surfaces treated with polymers. Particularly when used in factories/in the professional environment as few residues as possible are desirable on surfaces in order to avoid contamination of the particular work environment, for example, of workpieces, products and production equipment. Through a rapid absorption behaviour, it is possible to avoid negative effects also, therefore, such as leaving hydrophilic or emulsifying ingredients of compositions on water repellent surfaces, like surfaces to be painted. Thus, preferably, it is possible to reduce or completely avoid an undesired change of surfaces that come into contact with parts of the skin which have been treated with compositions of this invention when compared with known prior art compositions. In addition, residues on work pieces or products can be avoided or at least reduced, which could have a negative effect on the follow-up product during further processing. Also, the grip of the hands treated with the is compositions according to the invention is not or at least only minimally compromised.

DETAILED DESCRIPTION

The subject matters according to the invention are described below by way of example without the invention being restricted to these exemplary embodiments. Where ranges, general formulas or compound classes are given below, these are intended to include not only the corresponding ranges or groups of compounds that are explicitly mentioned but also all subranges and subgroups of compounds that can be obtained by extracting individual values (ranges) of compounds. If documents are cited in the present description, then their content, particularly with regard to the fact in whose connection the document was quoted, belongs fully to the disclosure content of the present invention. Where data is given in percentages, unless stated otherwise, they represent data expressed as percentages by weight. pH values were, unless otherwise stated, determined with commercially available pH meters based on potentiometry. If average values are given below, these represent weighted averages, if not indicated otherwise. If parameters are specified below, which were determined by measuring, the measurements were performed, unless otherwise stated, at a temperature of 25° C. and a pressure of 101.325 Pa.

The inventive compositions contain, as component a), 0.2 to 0.8% by wt., preferably 0.3 to 0.5% by wt. of at least one wax body, which is contained, either alone or in combination with one other or several other wax bodies. A wax body in the context of this invention includes all chemically modified, synthetic, vegetable and/or animal wax bodies. For example, included among the vegetable and/or animal wax components in particular are candelilla wax, carnauba wax, Japan wax, esparto, cork wax, rice germ oil wax, guarana wax, ouricury wax, montan wax, jojoba wax, argan wax, horseradish tree wax, olive wax, shea butter, berry wax, beeswax, grape seed wax, macadamia nut wax, sunflower wax, cotton seed wax, shellac wax, spermaceti, lanolin, rump fat; also mineral waxes, such as ceresin or ozokerite (earth wax); and the petrochemical waxes, such as petrolatum, paraffin waxes and microcrystalline waxes. Moreover, chemically modified wax bodies and synthetic wax bodies may be included as component a) in the compositions according to the invention, especially montan waxes, sasol waxes, hydrogenated jojoba waxes, in particular esters of jojoba oils, polyalkylene waxes, polyethylene glycol waxes, but also chemically modified waxes such as hydrogenated vegetable oil, in particular hydrogenated castor oil, hydrogenated coconut fatty glycerides, triglycerides, etc. Particularly preferably, the compositions according to the invention contain hydrogenated castor oil, which is marketed, for example, under the trademark CUTINA® HR by the Cognis company, or mineral waxes such as, for example, ceresin, which can be obtained as a microcrystalline wax under the trade designation Paracera® W 80. It has been found that compositions containing, as the wax body of the component a), 0.2 to 0.8% by wt., preferably 0.3 to 0.5% by wt. of at least one animal and/or vegetable wax, and at least one chemically modified wax body, have a particularly good absorption behaviour and a very good consistency. Quite excellent results were achieved particularly when the weight ratio of the total weight of the animal and vegetable wax bodies used to the total weight of the chemically modified waxy bodies used is between 1:2 and 2:1, and lies particularly preferably at 1:1.

The compositions according to the invention contain, as component b), 0.3 to 1% by wt., preferably 0.35 to 0.6% by wt. of at least one polymer based on at least one acrylic acid monomer and/or at least one ester of an acrylic acid monomer. The term polymer in the context of this invention includes both homopolymers and copolymers. Preferred polymers of component b) are particularly resistant to electrolytes and achieve stable compositions even in compositions with elevated salt concentrations. It is preferable that the polymer of component b) is an acrylic acid polymer. Preferred acrylic acid polymers in the context of this invention are all homopolymers of acrylic acids, or derivatives of acrylic acids such as copolymers of acrylic acid and/or derivatives of acrylic acid. The term derivative of acrylic acid comprises all chemically modified acrylic acids, especially esters of acrylic acid. Particularly preferred derivatives of acrylic acid are alkyl esters of acrylic acid, particularly preferably C10 to C30 alkyl esters of acrylic acid. Preferred polymers of acrylic acid are copolymers of acrylic acid and an ester of acrylic acid. Preferred homopolymers of acrylic acid are polymers known, for example, under the INCI name 'carbomers'. In a preferred embodiment, regarding the polymer of component b), acrylic acid polymers are involved, such as those distributed by Evonik Industries AG under the trade name Tego® Carbomer 141 or Tego® Carbomer 341 ER. These quoted embodiments, in combination with the other active ingredients of the groups of active ingredients a), c), d), e) and f), achieve exceptional stability of the total composition, and especially excellent absorption behaviour on the skin. Particular preference is given to acrylates/C10-30 alkyl acrylate crosspolymer, distributed, for example, by Evonik Industries AG under the trade name Tego® Carbomer 341 ER, since, with this active ingredient, particularly excellent results and very good stability of the composition can be achieved at a surprisingly low concentration of the polymer b), for example at a concentration of 0.3 to 0.4% by wt. It is particularly noteworthy that such polymers b) are stable even at an elevated electrolyte concentration, such as in the presence of salts, including, among others, sodium and/or potassium salts. In a particular embodiment, the polymer of component b) does not include homopolymer acrylic acids, such as those sold by Evonik Industries AG under the trade names Tego® Carbomer 134 or Tego® Carbomer 140.

Compositions, in which the weight ratio of the total weight of the wax component a) to the total weight of the polymer of the component b) is from 2:1 to 1:2, preferably 1:1, are, according to the invention, a preferred embodiment, since the absorption behaviour of such compositions on the skin is particularly excellent, with very good stability at the same time.

The inventive compositions contain, as component c), from 0.1 to 0.75% by wt., preferably 0.2 to 0.3% by wt. of at least one linear, saturated, unsubstituted fatty alcohol having 12 to 20 carbon atoms. According to the invention, fatty alcohols thus include primary alcohols having 12, 13, 14, 15, 16, 17, 18, 19 or 20 carbon atoms, which are exclusively hydrogen-substituted except for the —CH$_2$—OH group. The fatty alcohols with 16 and 18 carbon atoms, cetyl alcohol and stearyl alcohol, are preferred. Stearyl alcohol is particularly preferred. In combination with the other active ingredients of the drug groups a), b), d), e) and f), these embodiments achieve exceptional stability of the overall composition, and particularly excellent absorption behaviour on the skin, ensuring that the composition is experienced as non-aqueous and generous.

The inventive compositions contain, as component d), 6 to 12% by wt., preferably 7 to 10% by wt. of at least one emollient. For the purposes of the present invention, emollients are understood essentially to be all agents known to the skilled person which do not fall under any of the definitions of the other components a), b), c), e) or f) and which influence the sensory quality of a composition positively, that is to say, for example, making the epidermis of the skin smoother and softer. Preferred emollients may be selected from the group PEG-30 glyceryl cocoate, PEG-6 caprylic/capric glyceride, sorbitan sesquicaprylate, sucrose cocoate, isoamyl caproate, polyglyceryl-3 cocoate, PPG-3 myristyl ether, PPG-11 stearyl ether, cetearyl isononanoate, cetyl ethylhexanoate, caprylic/capric triglycerides, decal cocoate, diethylhexyl carbonates, decyl oleates, PPG-15 stearyl ether, octyl dodecanol, isocetyl palmitate, isohexadecane, cetearyl ethylhexanoate, isopropyl myristate, oleyl erucate, ethylhexyl palmitate, ethylhexyl stearate, isopropyl palmitate, PPG-14 butyl ether, triisostearin, C12-15 alkyl benzoate, cetyl ricenoleate, glyceryl ricenoleate, glyceryl stearate, isocetyl palmitate, isocetyl stearate, tocopheryl linoleate, methylheptyl isostearate, and mixtures thereof, with isoamyl cocoate particularly preferable. In combination with the other active ingredients of the groups of active ingredients a), b), c), e) and f), these embodiments achieve exceptionally good spreading behaviour of the total composition and particularly excellent absorption behaviour on the skin.

The inventive compositions contain, as component e), 0.5 to 1 5% by wt., preferably 0.8 to 1.2% by wt. of at least one ester having 20 to 34 carbon atoms selected from a linear, saturated, unsubstituted fatty acid and a linear, saturated, unsubstituted fatty alcohol. Within the scope of the invention, esters of a linear, saturated, unsubstituted fatty acid and a linear, saturated, unsubstituted fatty alcohol include, in this case, esters with 20, 21, 22, 23, 24, 25, 26, 27, 28, 29, 30, 31, 32, 33 or 34 carbon atoms, which are exclusively hydrogen-substituted except for the —COOCH$_2$— group. The distribution of carbon atoms in the fatty acid component and the fatty alcohol component can be in any manner. According to the invention, such esters are preferred in which the number of carbon atoms in the fatty acid component and the number of carbon atoms in the fatty alcohol component differ by not more than 5, preferably not more than 4, more preferably not more than 3, particularly not more than 2, particularly preferably not more than 1. Especially preferred are those esters in which the number of carbon atoms in the fatty acid component and the number of carbon atoms in the fatty alcohol component are the same. In combination with the other active ingredients of the groups to of active ingredients a), b), c), d) and f), these embodiments achieve exceptional stability of the total composition, a particularly excellent absorption behaviour and especially a silky feel to the skin. Preferred esters of component e) can be selected from cetyl palmitate, cetyl stearate, stearyl heptanoates, myristyl myristate, or mixtures thereof. Particularly preferred esters of component e) are selected from cetyl palmitate, cetyl stearate, myristyl myristate, or mixtures thereof, since, with these esters of component e), in each case the number of carbon atoms in the fatty acid component and the number of carbon atoms in the fatty alcohol component differ by not more 2. Particularly preferred also is the ester myristyl myristate with 14 carbon atoms each in the fatty acid component and the fatty alcohol component where the number of carbon atoms in the fatty acid component and the number of carbon atoms in the fatty alcohol component are the same.

The compositions according to the invention contain, as component f), at least one active ingredient selected from creatine, allantoin and/or glycerin. The total weight of active ingredients of component f) is preferably 0.2 to 8% by wt., preferably 1 to 6% by wt., more preferably 3 to 5% by wt., based on the total weight of the composition. Preferably, glycerin in amounts of less than 4% by wt., especially 1 to 4% by wt., may be used. In a preferred embodiment, the compositions comprise, as component f), glycerin and at least one further active ingredient selected from creatine and/or allantoin. Glycerin, creatine and allantoin are preferably used. In combination with the other active ingredients of the groups of active ingredients a), b), c), d) and e), these embodiments achieve exceptional stability of the total composition, and especially excellent absorption behaviour on the skin. Compositions in which the weight ratio of the total weight of creatine and allantoin to the total weight of glycerin is 1:6 to 1:2, preferably 1:3.2 to 1:3.6, achieve a particularly good moisturising effect on the skin. In particular, compositions that as component f) contain creatine, allantoin and glycerin in the indicated weight ratios achieve remarkably good moisturising effects.

Each of the listed preferred embodiments of the agent groups a) to f) and the preferred weight ratios quoted, is inherently preferred in a composition according to the invention. Any combinations that result from a composition according to the invention with one or more preferred embodiment (s) of the active ingredient groups a) to f) and/or with the stated preferred weight ratios shown also come under the present invention and are hereby explicitly included in addition to the quoted preferred embodiments.

In the event that there should be some overlaps of individual active ingredients of the active ingredient groups a) to f), all active ingredients involving a linear, saturated, unsubstituted fatty alcohol having 12 to 20 carbon atoms are assigned to group c) and all active ingredients involving an ester having 20 to 34 carbon atoms composed of a linear, saturated, unsubstituted fatty acid and a linear, saturated, unsubstituted fatty is alcohol are assigned to group e). An assignment of these agents to other active ingredient classes is not within the scope of this invention. The assignment of active ingredients to the active ingredient groups a) to f) is carried out according to the invention in the order f), c), e), b), a), d). The reassigned active ingredient group must be taken into account only when an active ingredient group cannot be assigned to any of the preceding active ingredient groups. Otherwise, the active ingredient is assigned to the first matching active ingredient group in the appropriate order.

Preferred compositions according to the invention have a pH value less than 7 More preferably, the compositions have a pH value between 4.5 and 6.0 and more preferably between 5.0 and 5.5.

Preferably, the compositions according to the invention have a viscosity from 5000 to 100,000 mPa·s, more preferably 8000 to 50,000 mPas·s, particularly preferably from 10,000 to 25,000 mPas·s measured using a viscometer by Brookfield Engineering Inc., namely, a Brookfield RVT rotation viscometer with spindle set 1-7.

Preferred compositions contain as an active ingredient combination, based on the total weight of the composition
a) 0.3 to 0.5% by wt. of at least one wax body;
b) 0.35 to 0.5% by wt. of at least one polymer based on at least one acrylic acid monomer and/or at least one ester of an acrylic acid monomer;
c) from 0.2 to 0.3% by wt. of at least one linear, saturated, unsubstituted fatty alcohol having 12 to 20 carbon atoms;
d) 7 to 10% by wt. of at least one emollient;
e) 0.8 to 1.2% by wt. of at least one linear, saturated, unsubstituted ester having 20 to 34 carbon atoms of a fatty acid and a fatty alcohol and
f) 0.2 to 8% by wt. of at least one active ingredient selected from creatine, allantoin to and/or glycerin.

In a preferred embodiment, the compositions contain as an active ingredient combination, based on the total weight of the composition a) 0.2 to 0.8% by wt., preferably 0.3 to 0.5% by wt. of at least one animal and/or vegetable wax body and at least one chemically modified wax body wherein the weight ratio of the total weight of the animal and vegetable wax body(ies) used to the total weight of the chemically modified wax body(ies) used is 1:2 to 2:1, preferably 1:1;
b) 0.3 to 1% by wt., preferably from 0.35 to 0.5% by wt. of at least one polymer based on at least one acrylic acid monomer and/or at least one ester of an acrylic acid monomer selected from homopolymers of acrylic acid and/or copolymers of acrylic acid and/or alkyl esters of acrylic acid, preferably 010 to C30 alkyl esters of acrylic acid, and particularly preferably acrylates/C10-30 alkyl acrylate crosspolymer;
c) 0.1 to 0.75% by wt., preferably 0.2 to 0.3% by wt. of at least one linear, saturated, unsubstituted fatty alcohol having 16 to 18 carbon atoms selected from stearyl alcohol and cetyl alcohol;
d) 6 to 12% by wt., preferably 7 to 10% by wt. of at least one emollient selected from PEG-30 glyceryl cocoate, PEG-6 caprylic/capric glyceride, sorbitan sesquicaprylate, sucrose cocoate, isoamyl caproate, polyglyceryl-3 cocoate, PPG-3 myristyl ether, PPG-1 1 stearyl ether, cetearyl isononanoate, cetyl ethylhexanoate, caprylic/capric triglyceride, decal cocoate, diethylhexyl carbonates, decyl oleate, PPG-15 stearyl ether, octyl dodecanol, isocetyl palmitate, isohexadecane, cetearyl ethyl hexanoate, isopropyl myristate, oleyl erucate, ethylhexyl palmitate, ethylhexyl stearate, isopropyl palmitate, PPG-14 butyl ether, triisostearin, C12-15 alkyl benzoate, cetyl ricenoleate, glyceryl ricenoleate, glyceryl stearate, isocetyl palmitate, isocetyl stearate, tocopheryl linoleate, methylheptyl isostearate and mixtures therefrom, most preferably isoamyl cocoate;
e) 0.5 to 1.5% by wt., preferably 0.8 to 1.2% by wt. of at least one ester having 24 to 32, preferably 28, carbon atoms, of a linear, saturated, unsubstituted fatty acid and a linear, saturated, unsubstituted fatty alcohol, wherein the number of carbon atoms in the fatty acid component and the number of carbon atoms in the fatty alcohol component differ by not more than 2, preferably not more than 1, more preferably by no carbon atom (s), preferably selected of cetyl palmitate, cetyl stearate, myristyl myristate, and mixtures thereof, most preferably myristyl myristate and
f) 0.2 to 8 parts % by wt., preferably 1 to 6% by wt., more preferably 3 to 5% by wt. of at least one active ingredient selected from creatine, allantoin and/or, preferably and, glycerin,
wherein the composition contains no other substances, which fall within the groups of is active ingredients referred to in the groups a) to f). These compositions have exceptional stability of the total composition and particularly excellent absorption behaviour on the skin. Therefore, they leave very little residues on surfaces, especially water-repellent surfaces. In addition, these compositions according to the invention are especially easily spreadable, they are non-sticky, and the composition is stable during application on the skin, that is, the composition does not break down.

In addition to the active ingredient combinations of the active ingredients a) to f), if desired, the composition can contain other active ingredients.

In a preferred embodiment, the composition further contains urea, preferably in quantities of 0.0001 to 5% by wt., particularly preferably 0.001 to 2.5% by wt., based on the total weight of the composition.

Preferably also, such compositions may also contain the active ingredient polyglyceryl-3-dicitrate/stearate.

Preferable compositions of this type are those also containing the active ingredients polyglyceryl-3 dicitrate/stearate and urea. In a particular embodiment, compositions according to the invention contain polyglyceryl-3-dicitrate/stearate and urea in a weight ratio of from 100:1 to 150:1, preferably 125:1. Compositions containing polyglyceryl-3-dicitrate/stearate and urea in these weight ratios are surprisingly very stable and are particularly moisturising on the skin with very good absorption behaviour on the skin.

Those compositions may also be preferable that further contain the active ingredient betaine, also known under the name trimethylglycine. While maintaining good stability, such compositions can give an especially intensive care impression.

Also preferable are such compositions that contain the active ingredients betaine and urea. Betaine and urea are especially preferred in a weight ratio of 4:1 to 1:1, more preferably of 2:1. Compositions containing betaine and urea in these weight ratios are particularly moisturising to the skin.

Preferred compositions of the invention contain at least 70% by wt., preferably at least 75% by wt., more preferably at least 80% by wt. of water.

In the case of the compositions according to the invention, cosmetic and/or dermatological formulations are preferably involved which may exist in general as aqueous-alcoholic solutions, creams, emulsions, lotions, gels, aerosol sprays or foams, is non-aerosol sprays or foams. Preferably, creams and/or lotions are involved. Particularly preferred are hydrophilic creams and/or lotions which can exist as an oil in water emulsion (O/W emulsion).

The compositions according to the invention may optionally contain other components commonly used in cosmetic and/or dermatological formulations. Further preferred components may be selected from the group consisting of fragrances and perfumes, preservatives and/or pH balancing agents, such as aqueous sodium hydroxide solution.

The compositions according to the invention may also include other conventional ingredients for adapting which are used to treat, care, cleanse and protect the skin, such as cosmetic skin active ingredients. The term cosmetic skin ingredients within the context of this invention comprises, for example, ceramides, pseudoceramides, protein hydrolysates of plant or animal origin based on keratin, collagen, elastin, wheat, rice, soy, milk, silk, corn, amino acids and amino acid derivatives, anti-inflammatory agents, antimicrobial agents, conventional antioxidants, vitamins, dexpanthenol, lactic acid, pyrrolidonecarboxylic acid, bisabolol, as well as plants, yeast, and/or extracts of algae.

A combination with commonly used organic or inorganic UV filters is also possible and is regarded in sunscreen preparations, for example, as particularly advantageous, since, during the application, the drying of the skin can be effectively prevented and thereby can maintain the natural protective function of the skin. In addition, further cosmetic supplements and additives which are customary in such preparations, may be included. Such supplements are, for example, solubilisers such as ethanol, isopropanol, ethylene glycol; propylene glycol and diethylene glycol. Additional components include cosmetic oils of vegetable and synthetic origin, silicone oils, greases, moisturising agents, emulsifiers, anionic, zwitterionic, ampholytic and nonionic surfactants and/or to colouring agents.

Finally, the formulations of this invention can also contain complex formers, such as EDTA, NTA, β-alanine diacetic acid and phosphonic acids, dyes for colouring the cosmetic preparation, opacifiers, such as latex, styrene, and styrene-acrylamide copolymers, ceramides, β-glucanes, oligopeptides, hyaluronic acid, pearlising agents such as ethylene glycol mono- and distearate and PEG-3 distearate, pigments, light stabilisers, thickening agents or propellants.

In a preferred embodiment, compositions according to the invention are free of compounds selected from silicone compounds, dipropylene glycol, paraben and/or alkyl parabens, formaldehyde releasers, such as diazolidinyl urea, imidazolidinyl urea and/or DMDM hydantoin, preservatives based on organic halogen compounds such as, for example, triclosan, and mixtures thereof. Particularly preferred are compositions according to the invention that are free of paraben and/or alkyl parabens, more preferably, free of paraben and alkyl parabens. Included under the designations paraben and alkyl parabens within the context of the invention are, in particular, 4-hydroxybenzoic acid and 4-hydroxybenzoic acid esters, such as methyl 4-hydroxybenzoate, ethyl 4-hydroxybenzoate, propyl 4-hydroxybenzoate and/or butyl-4-hydroxybenzoate. Also particularly preferred are those compositions according to the invention that are free of silicone compounds. This may be particularly desirable when the compositions are used in the work environment with sensitive surfaces, such as surfaces to be painted, since silicone compounds could potentially leave residues on workpieces or products, which could have a negative effect on the product during further processing. In a particularly preferred embodiment, compositions according to the invention may be free of silicone compounds and free of paraben and free of alkyl parabens.

The compositions according to the invention may be prepared in any fashion. Preferably, compositions of the invention are obtainable by the method according to the invention described below.

Another objective of the present invention, therefore, is to provide methods for preparing compositions comprising
a) at least one wax body
b) at least one polymer based on at least one acrylic acid monomer and/or at least one ester of an acrylic acid monomer
c) at least one linear, saturated, unsubstituted fatty alcohol having 12 to 20 carbon atoms
d) at least one emollient
e) at least one linear, saturated, unsubstituted ester having 20 to 34 carbon atoms of a fatty acid and a fatty alcohol and
f) at least one active ingredient selected from creatine, allantoin and/or glycerin comprising the following steps:
i) preparing a first phase, by mixing the active ingredients a), c), a first part of d), as well as e);
ii) preparing a second phase by mixing at least one of the active ingredients mentioned under f) with water;
iii) preparing a third phase by mixing the active ingredients b) and the remaining part of d);
iv) homogenising the first and the second phase by stirring;
v) mixing the composition obtained in step iv) with the third phase;
vi) optionally, adding perfume, preservative, betaine, urea and/or other substances to the composition obtained in step v) and
vii) balancing the pH value.

In a particular embodiment of the present invention, the method for preparing compositions comprising
a) at least one wax body;
b) at least one polymer based on at least one acrylic acid monomer and/or at least one ester of an acrylic acid monomer;
c) at least one linear, saturated, unsubstituted fatty alcohol having 12 to 20 carbon atoms;

d) at least one emollient;
e) at least one linear, saturated, unsubstituted ester having 20 to 34 carbon atoms of a fatty acid and a fatty alcohol and
f) at least one active ingredient selected from creatine, allantoin and/or glycerin, comprises the following steps:
i) preparing a first phase, by mixing the active ingredients a), c), a first part of d), as well as e) and heating the phase to over 65° C. while stirring;
ii) preparing a second phase by mixing at least one of the active ingredients mentioned under f) with water and heating to over 70° C. while stirring;
iii) preparing a third phase by mixing the active ingredients b) and the remaining part of d), and heating the phase to over 65° C. while stirring;
iv) homogenising the first and the second phase by stirring at a temperature greater than 60° C.;
v) mixing the composition obtained in step iv) with the third phase at a temperature below 65° C.;
vi) optionally, adding perfume, preservative, betaine, urea and/or other substances to the composition obtained in step v) at a temperature less than 60° C., preferably less than 45° C., while stirring;
vii) balancing the pH while stirring and
viii) optionally, venting the composition at room temperature In a further particular embodiment of the present invention, the method for preparing compositions comprising
a) 0.2 to 0.8% by wt. of at least one wax body
b) 0.3 to 1% by wt. of at least one polymer based on at least one acrylic acid monomer and/or at least one ester of an acrylic acid monomer,
c) 0.1 to 0.75% by wt. of at least one linear, saturated, unsubstituted fatty alcohol having 12 to 20 carbon atoms
d) 6 to 12% by wt. of at least one emollient
e) from 0.5 to 1.5% by wt. of at least one linear, saturated, unsubstituted ester having 20 to 34 carbon atoms of a fatty acid and a fatty alcohol, and
f) at least one active ingredient selected from creatine, allantoin and/or glycerin, comprises the steps
i) preparing a first phase, by mixing the active ingredients a), c), a first part of d), as well as e) and heating the phase to a temperature of over 65° C. while stirring,
ii) preparing a second phase by mixing at least one of the active ingredients mentioned under f) with water and heating to over 60° C. while stirring
iii) preparing a third phase by mixing the active ingredients b) and the remaining part of d), and heating the phase to over 65° C. while stirring
iv) homogenising the first and the second phase by stirring at a temperature greater than 60° C.
v) mixing the composition obtained in step iv) with the third phase at a temperature below 65° C.
vi) optionally, adding perfume, preservative, betaine, urea and/or other substances to the composition obtained in step v) at a temperature less than 60° C., preferably less than 45° C., while stirring,
vii) balancing the pH while stirring.
viii) venting the composition at room temperature The first phase of the composition, in step i) of the manufacturing process, is heated to a temperature of over 65° C., preferably of over 70° C., especially 75-80° C.

The second phase of the composition, in step ii) of the manufacturing process, is heated to a temperature of over 60° C., preferably of over 65° C., especially 70-75° C.

The temperature in step v) of the production process is preferably less than 65° C., in particular 60° C.

The temperature in step vi) of the production process is preferably less than 60° C., more preferably less than 45° C. and especially 40° C.

Preferably, stirring in the steps iv), v) and vii) of the production method in each case lasts for 2 to 20 minutes, preferably at least 5 minutes.

By adjustment of the corresponding quantities, and using the appropriate ingredients, any composition of the invention can be produced by this method.

Compositions according to the invention or produced according to the invention are preferably applied as a cream, lotion or gel on the human skin. Further to this, another objective of the present invention is the use of compositions according to the invention for topical application to the skin. Preferably, each part of the skin such as, for example, the face, hands, forearms, and the entire human body, can are treated with compositions according to the invention. Preference is given the treatment of hands, forearms and face, especially the hands and forearms, with compositions according to the invention. This includes any form of administration of compositions to the skin according to the invention. Examples of possible applications are the application with hands and with auxiliary devices, creaming, rubbing, spraying and massaging.

Another objective of the present invention is therefore the use of compositions according to the invention as a skin cream, in particular a cream for the hands and forearms.

Another object of the present invention is the cosmetic use of compositions according to the invention for the care of the skin.

Another objective of the present invention is the cosmetic use of compositions according to the invention as a moisturiser for the skin. Preferably, the cosmetic use of compositions according to the invention can be as a long-lasting moisturiser for the skin. A long-lasting moisturiser for the skin can exist according to the invention if skin moisture measurements, in particular according to Example 4, confirm the moisturising effect.

Another objective of the present invention is the cosmetic use of compositions according to the invention for the reduction of a rough, dry and/or tight skin sensation. The reduction of a rough, dry and/or tight skin sensation can exist according to the invention if the subjective perception of the test person involved confirms this.

In particular, in daily work, the skin is highly stressed by environmental factors and work-related influences. Another objective of the present invention is therefore the use of cosmetic compositions according to the invention on stressed skin. A preferred embodiment of the present invention, furthermore, is the cosmetic use of compositions according to the invention for the protection of stressed skin.

Another objective of the present invention is the cosmetic use of compositions according to the invention on normal skin.

Another objective of the present invention is the cosmetic use of compositions according to the invention for daily use.

Another objective of the present invention is the cosmetic use of compositions according to the invention for daily use under normal occupational stress. For the purposes of this invention, normal occupational stress is understood to mean, for example, office work, production, sales, craft activity, simple laboratory activity, outdoor activity under normal climatic conditions such as temperatures between 0° C. and 30° C., occasional contact with water or cleansing agents, the occasional wearing of gloves, which can lead to softening of the skin, and all everyday professional work in which normal influences, as opposed to extreme conditions, affect the skin, such as extreme is cold well below 0° C., extreme heat, well above 40° C., continuous skin contact with chemicals, such as formaldehyde, chemical agents or cleansing agents or exposure to UV radiation.

Of course, the uses listed may also occur simultaneously or may overlap. A preferred use may be, therefore, the preferred daily use of the compositions according to the invention as a skin cream for topical application to the skin, particularly as a cream for the hands and forearms, for use on stressed or normal skin under normal occupational stress and/or for caring and/or as a moisturiser, particularly a long-lasting moisturiser for the skin and/or for the protection of stressed skin and/or for the reduction of a rough, dry and/or tight skin sensation.

The invention is illustrated by way of examples. These explanations are merely exemplary, and do not limit the present invention.

Example 1: Preparation of Compositions

The compositions listed in Table 1 are prepared according to the described manufacturing method:
i) preparing a first phase, by mixing the active ingredients a), c), a first part of d), as well as e) and heating the phase to a temperature of over 65° C. while stirring,
ii) preparing a second phase by mixing at least one of the active ingredients mentioned under f) with water and heating to over 60° C. while stirring
iii) preparing a third phase by mixing the active ingredients b) and the remaining part of d), and heating the phase to over 65° C. while stirring
iv) homogenising the first and the second phase by stirring at a temperature greater than 60° C.
v) mixing the composition obtained in step iv) with the third phase at a temperature below 65° C.
vi) optionally, adding perfume, preservative, betaine, urea and/or other substances to the composition obtained in step v) at a temperature less than 60° C., preferably less than 45° C., while stirring,
vii) balancing the pH while stirring.
viii) venting the composition at room temperature
with the active ingredients a) to f) defined as in the specification and defined in greater detail in Table 1.

In the compositions, E1 and E2 are creams according to the invention. The comparison tests V1 to V10 show compositions which do not fall under the subject matter of the invention.

Example 2: Stability Tests

The different compositions were first assessed for their stability. For this purpose, the compositions to be tested were stored for a period of 3 months, at temperatures respectively of 4° C., 20 to 25° C. (room temperature) as well as at 40° C. and subsequently checked for consistency. The stability was evaluated based on the following criteria:
Stable: no visible phase separation, no precipitation of solids, unchanged consistency, unchanged colour, unchanged odour
Less stable: easily visible phase separation, partial precipitation of solids, slightly changed consistency, slight change in colour, slight change in odour,
unstable: clearly visible phase separation, visible precipitation of solids, significantly changed consistency, significant colour change, marked change of odour right up to the perception of a bad smell
The results of the stability tests are listed in Table 1.

Example 3: Subjective Assessment of Effectiveness and Efficacy

The different compositions were then evaluated by a test panel of 15 men and women with healthy skin according to their reactivity and their nourishing/care properties with dermal application on the volar forearm and on the hands. The results are also shown in Table 1.

The products were rated into the categories very good, good and bad according to their absorption behaviour.

The nourishing properties were first classified according to a positive, neutral or negative impression and then the perceived effect was determined. The following impressions were majority-based: strong care impression, no care impression, aqueous impression of the product (which is often caused by the breakdown of the composition during application), occlusive impression of the product.

All data refer to, unless otherwise stated, a weight percent based on the total weight of the composition. Likewise, all the specified ratios are to be understood as the weight ratios of the respective ingredients.

TABLE 1

| Part 1 | | | | | | |
|---|---|---|---|---|---|---|
| | E1 | E2 | V1 | V2 | V3 | V4 |
| Isoamylcocoate | 4.5 | 4.23 | 4.5 | 4.5 | 4.5 | 4.5 |
| Glycerin | 3.0 | 3.4 | 3.0 | 3.0 | 3.0 | 3.0 |
| Caprylic/capric triglycerides | 3.5 | 3.25 | 3.5 | 3.5 | 3.5 | 3.5 |
| Polyglyceryl-3 dicitrate/stearate | 2.5 | 2.5 | 2.5 | 2.5 | 2.5 | 2.5 |
| Myristyl myristate | 1.0 | 1.0 | 1.0 | 1.0 | 1.0 | 1.0 |
| Allantoin | 0.5 | 0.5 | 0.5 | 0.5 | 0.5 | 0.5 |
| Creatine | 0.5 | 0.5 | 0.5 | 0.5 | 0.5 | 0.5 |
| Stearyl alcohol | 0.3 | 0.25 | 0.3 | 0.3 | 0.3 | 0.8 |
| Hydrogenated castor oil (HYDROGENATED CASTOR OIL) | 0.25 | 0.2 | 0.8 | — | 0.25 | 0.25 |
| Cera Microcristallina/paraffin | 0.25 | 0.2 | 0.2 | 0.18 | 0.25 | 0.25 |
| Acrylates/C 10-30 alkyl acrylate crosspolymer | 0.5 | 0.4 | 0.5 | 0.5 | 0.15 | 0.5 |

TABLE 1-continued

|  | | | | | | |
|---|---|---|---|---|---|---|
| Perfume, preservative pH balancing agents, urea, betaine, more ingredients | 0.5-3 | 0.5-3 | 0.5-3 | 0.5-3 | 0.5-3 | 0.5-3 |
| Water | to 100 | to 100 | to 100 | to 100 | to 100 | to 100 |
| Ratio of glycerin to allantoin and creatine | 3.3:1 | 3.4:1 | 3.3:1 | 3.3:1 | 3.3:1 | 3.3:1 |
| Ratio polyglyceryl-3 dicitrate/stearate urea | 125:1 | 125:1 | 125:1 | 125:1 | 125:1 | 125:1 |
| Ratio of betaine to urea | 2:1 | 2:1 | 2:1 | 2:1 | 2:1 | 2:1 |
| Ratio chemically modified wax body to animal/vegetable wax component | 1:1 | 1:1 | 4:1 | — | 1:1 | 1:1 |
| Overall ratio wax body a) polymer b) | 1:1 | 1:1 | 2.5:1 | 1:2.2 | 1:1 | 1:1 |
| Absorption behaviour | v. good | v. good | bad | good | good | bad |
| Stability of the little composition | stable | stable | stable | unstable | unstable | less stable |
| Impression on the skin care/haptics | positive/ strong care impression | positive/ strong care impression | negative/ occlusive impression of product | negative/ acqueous impression of product, low viscosity | neutral/ acqueous impression, good care impression | negative/ occlusive impression of product |

Part 2

|  | V5 | V6 | V7 | V8 | V9 | V10 |
|---|---|---|---|---|---|---|
| Isoamylcocoate | 4.5 | 6.5 | 2.5 | 4.5 | 4.5 | 4.5 |
| Glycerin | 3.0 | 3.0 | 3.0 | 3.0 | 3.0 | 4.2 |
| Caprylic/capric triglycerides | 3.5 | 6.5 | 2.5 | 3.5 | 3.5 | 3.5 |
| Polyglyceryl-3 dicitrate/stearate | 2.5 | 2.5 | 2.5 | 3.0 | 3.0 | 3.0 |
| Myristyl myristate | 1.0 | 1.0 | 1.0 | 1.6 | 0.4 | 1.0 |
| Allantoin | 0.6 | 0.6 | 0.6 | 0.6 | 0.6 | — |
| Creatine | 0.6 | 0.6 | 0.6 | 0.6 | 0.6 | — |
| Stearyl alcohol | 0.08 | 0.3 | 0.3 | 0.3 | 0.3 | 0.3 |
| Hydrogenated castor oil (HYDROGENATED CASTOR OIL) | 0.25 | 0.25 | 0.25 | 0.25 | 0.25 | 0.25 |
| Cera Microcristallina/ paraffin | 0.25 | 0.25 | 0.25 | 0.25 | 0.25 | 0.25 |
| Acrylates/C 10-30 alkyl acrylate crosspolymer | 0.5 | 0.5 | 0.5 | 0.5 | 0.5 | 0.5 |
| Perfume, preservative pH balancing agents, urea, betaine, more ingredients | 0.5-3 | 0.5-3 | 0.5-3 | 0.5-3 | 0.5-3 | 0.5-3 |
| Water | to 100 | to 100 | to 100 | to 100 | to 100 | to 100 |
| Ratio of glycerin to allantoin and creatine | 3.3:1 | 3.3:1 | 3.3:1 | 3.3:1 | 3.3:1 | 7:1 |
| Ratio polyglyceryl-3 dicitrate/stearate urea | 125:1 | 125:1 | 125:1 | 125:1 | 125:1 | 125:1 |
| Ratio of betaine to urea | 2:1 | 2:1 | 2:1 | 2:1 | 2:1 | 2:1 |
| Ratio chemically modified wax body to animal/vegetable wax component | 1:1 | 1:1 | 1:1 | 1.1 | 1:1 | 1:1 |
| Overall ratio wax body a) polymer b) | 1:1 | 1:1 | 1:1 | 1.1 | 1:1 | 1:1 |
| Absorption behaviour | bad | bad | good | bad | bad | good |

TABLE 1-continued

| Stability of the little composition | less stable | stable | stable | less stable | less stable | stable |
|---|---|---|---|---|---|---|
| Impression on the skin care/haptics | negative/ no care impression | negative/ no care impression | negative/ no care impression | negative/ occlusive impression of product, | negative/ no care impression | negative/ no care impression |

The experiments clearly show that only with compositions according to the invention can a completely satisfactory result be achieved in the skin in terms of stability of the composition and impression on the skin and absorption behaviour. The rapid absorption behaviour, in addition to the pleasant, caring, non-sticky feeling by the test subjects, has the positive effect that contact with surfaces by those parts of the skin treated with compositions according to the invention cause significantly fewer unwanted residues on the respective surfaces, such as plastic surfaces, for example, a keyboard and telephone, glass surfaces, plexiglass or modified glass surfaces, surfaces to be painted, lacquers, especially automotive lacquers, varnishes, ceramics, porcelain, metal, alloys, laboratory materials or surfaces treated with polymers, than is the case with non-inventive compositions.

Example 4: Effectiveness and Efficiency—Moisturising Effect

In addition to the subjective impression of the test subjects, the cream E2 according to the invention was also tested for its effectiveness and efficiency. For this purpose, the determination of TEWL (transepidermal water loss) and skin moisture were selected as is measurable parameters. The comparison was made over a period of 14 days between the arm (dermal application on the volar forearm) treated with cream with and the arm, not treated with cream, from a test panel of 15 men and women with healthy skin.

To determine the initial value of TEWL and skin moisture, a test area (approximately 4×4 cm) was marked on the underside of the right and left arm of each subject using a template. Within this test area, determinations in triplicate of TEWL and quintuple determinations of skin hydration were performed (day 0). The TEWL was determined using a multi probe adapter MPA 5 with Tewameter® TM300 probe and the skin moisture with a multi probe adapter MPA 5 with Corneometer® probe CM 825. The measurements were performed at 20° C. and 40% relative humidity. Immediately after the measurements, application of the cream was carried out, each time with always the left arm of each subject getting creamed with the test cream in the morning and evening, with the right arm remaining free of any cream during the entire test period (negative control).

Further determinations of TEWL and skin moisture were made as described above on day 7 and day 14, in which the morning application of the lotion on the morning of the measurement day took place only after determination of TEWL and skin moisture so as not to capture any water in the measurements which was possibly evaporating from the cream.

The mean values and the standard deviation from the measured values of the test panel of 15 persons and the respective triplicate (TEWL) or five-fold determination (skin hydration) of the right and left arm of each subject on day 0, day 7 and day 14 were calculated. The results of the TEWL are shown in Table 2, and the results of skin to moisture measurements are shown in Table 3:

TABLE 2

Results of TEWL

| | before application | Day 7 | Day 14 |
|---|---|---|---|
| Left arm | 7.4 ± 0.8 | 6.1 ± 0.8 | 6.1 ± 0.8 |
| Right arm | 6.5 ± 0.8 | 6.0 ± 0.8 | 6.1 ± 0.8 |

TABLE 3

Results of skin moisture measurements

| | before application | Day 7 | Day 14 |
|---|---|---|---|
| Left arm | 31.9 ± 2 | 35.8 ± 2 | 38.1 ± 2 |
| Right arm | 30.5 ± 2 | 29.7 ± 2 | 32.4 ± 2 |

Both on the right arm (without cream) and the left arm (with cream), the TEWL remained after 14 days within the range of the standard deviation with no appreciable difference. The measurement of skin moisture also remained, after 14 days on the right arm (without cream), within the range of the standard deviation with no appreciable difference.

The significant increase in skin moisture of 19.4% on the left arm (with cream) compared to the right arm clearly shows the effectiveness and the moisturising effect of the composition according to the invention, by means of which the good care of the skin in particular happens in the face of everyday influences. Therefore, the compositions of this invention are particularly well suited for daily use in normal everyday stress of the skin. Experiments with other compositions according to the invention lead to very similar results.

Example 5: Skin Compatibility

Cream E2 according to the invention was also tested for skin compatibility. The test was performed with a test panel of 21 men and women with healthy skin. First, a test area for each test substance was marked on the forearms and then skin in these test areas was pre-damaged by scoring with a sterile needle. About 0.2 g of the test substance was filled into a Finn chamber, applied to the test surfaces of the forearm and fixed for 23 hours. After 23 hours, the Finn chamber was removed and rinsing with tap water was performed by the subject. An hour later the inspection (visual score) of the test fields took place. The application was carried out on three successive days. As a control, Vaseline DAB 10 was tested as described above.

Calculation and Evaluation

The visual score was calculated daily 1 hour after removal of the chambers and is shown in Table 4.

TABLE 4

| Visual score | |
|---|---|
| Symptoms/assessment of the scarification points | Visual score x |
| Negative | 0 |
| Reddening limited to scratches | 1 |
| Wide bands, increased reddening with/without blisters, (clear fluid), pustules (pus) or erosions | 2 |
| Severe erythema with coalescence in places with/without other lesions | 3 |
| Coalescing severe erythema, oedema, necrosis, blister formation | 4 |

If a rating lay between two rating points, it was possible to differentiate the assessment further in increments of 0.5 or smaller.

For the evaluation of the relative skin compatibility of the test products, the average of the visual score was derived from values x with regard to the average application time. These values are shown in Table 5 for E1 and the standard Vaseline, DAB 10.

TABLE 5

| Results of skin compatibility | | |
|---|---|---|
| | Mean visual score values x | Mean duration of application |
| Cream E1 | 0.4 | 63.5 h |
| Standard Vaseline | 0.5 | 63.5 h |

Tests with other compositions according to the invention lead to very similar results. These results show that compositions according to the invention are extremely skin-friendly and will not lead to significant skin irritation. At the same application time, compositions according to the invention perform just as well or tend to be slightly better in the skin compatibility test than the standard Vaseline DAB 10.

Similar testing reports are known in the art and are published, for example, under P. J. Frosch, A. M. Kligman, Contact Dermatitis, 5, 73 (1979); P. J. Frosch, A. M. Kligman, J. Am. Acad. Dermatol., 1, 35 (1979) or P. J. Frosch, A. M. Kligman, Contact Dermatitis, 2, 314 (1976). The contents of these references are incorporated herein in their entirety.

The invention claimed is:

1. Cosmetic and/or dermatological composition, comprising, as a combination of active ingredients, and based on the total weight of the particular composition
   a) 0.2 to 0.8% by wt. of at least one wax body selected from petrochemical waxes and hydrogenated vegetable oil;
   b) 0.3 to 1% by wt. of at least one polymer based on at least one acrylic acid monomer and/or at least one ester of an acrylic acid monomer selected from homopolymers of acrylic acid and/or copolymers of acrylic acid and/or alkyl esters of acrylic acid;
   c) 0.1 to 0.75% by wt. of at least one linear, saturated, unsubstituted fatty alcohol having 12 to 20 carbon atoms;
   d) 6 to 12% by wt. of at least one emollient selected from PEG-30 glyceryl cocoate, PEG-6 caprylic/capric glyceride, sucrose cocoate, isoamyl caproate, isoamyl cocoate, polyglyceryl-3 cocoate, caprylic/capric triglyceride, decal cocoates, and mixtures therefrom;
   e) from 0.5 to 1.5% by wt. of at least one linear, saturated, unsubstituted ester selected from cetyl palmitate, cetyl stearate, myristyl myristate, stearyl hepanoates and mixtures thereof;
   f) at least one active ingredient selected from creatine and/or allantoin; and
   g) glycerin in which the weight ratio of the total weight of creatine and allantoin to the total weight of glycerin is 1:6 to 1:2.

2. Composition of claim 1 comprising as an active ingredient combination, based on the total weight of the composition
   a) 0.3 to 0.5% by wt. of at least one wax body selected from petrochemical waxes and hydrogenated vegetable oil;
   b) 0.35 to 0.5% by wt. of at least one polymer based on at least one acrylic acid monomer and/or at least one ester of an acrylic acid monomer selected from homopolymers of acrylic acid and/or copolymers of acrylic acid and/or alkyl esters of acrylic acid;
   c) from 0.2 to 0.3% by wt. of at least one linear, saturated, unsubstituted fatty alcohol having 12 to 20 carbon atoms;
   d) 7 to 10% by wt. of at least one emollient selected from PEG-30 glyceryl cocoate, PEG-6 caprylic/capric glyceride, sucrose cocoate, isoamyl caproate, isoamyl cocoate, polyglyceryl-3 cocoate, caprylic/capric triglyceride, decal cocoates, and mixtures therefrom;
   e) from 0.8 to 1.2% by wt. selected from cetyl palmitate, cetyl stearate, myristyl myristate, stearyl hepanoates;
   f) from 0.2 to 8 parts by % by wt. of at least one active ingredient selected from creatine and/or allantoin; and
   g) glycerin in which the weight ratio of the total weight of creatine and allantoin to the total weight of glycerin is 1:6 to 1:2.

3. Composition according to claim 1, containing as active ingredients a) to g)
   a) least one wax body selected from petrochemical waxes and hydrogenated vegetable oil;
   b) at least one polymer based on at least one acrylic acid monomer and/or at least one ester of an acrylic acid monomer selected from homopolymers of acrylic acid and/or copolymers of acrylic acid and/or alkyl esters of acrylic acid;
   c) at least one linear, saturated, unsubstituted fatty alcohol having 16 to 18 carbon atoms selected from stearyl alcohol and cetyl alcohol;
   d) at least one emollient selected from PEG-30 glyceryl cocoate, PEG-6 caprylic/capric glyceride sucrose cocoate, isoamyl caproate, polyglyceryl-3 cocoate, caprylic/capric triglyceride, decal cocoates, and mixtures therefrom;
   e) at least one ester selected from cetyl palmitate, cetyl stearate and myristyl myristate, wherein the number of carbon atoms in the fatty acid component and the number of carbon atoms in the fatty alcohol component differ by not more than 2;
   f) at least one active ingredient selected from creatine and/or allantoin; and
   g) glycerin in which the weight ratio of the total weight of creatine and allantoin to the total weight of glycerin is 1:6 to 1:2.

4. Composition according to claim 1, comprising creatine, allantoin and glycerin.

5. Composition according to claim 1, wherein the weight ratio of the total weight of the wax component a) to the total weight of the polymer of component b) is from 2:1 to 1:2.

6. Composition according to claim 1, wherein the composition further contains the active ingredients polyglyceryl-3-dicitrate/stearate and urea.

7. Composition according to claim 6 wherein polyglyceryl-3 dicitrate/stearate and urea are used in a weight ratio of from 100:1 to 150:1.

8. Composition according to claim 1, further comprising the active ingredients betaine and urea, wherein betaine and urea can be used in a weight ratio of 1:4 to 1:6.

9. Composition according to claim 1, wherein the composition further comprises at least 70% by wt., of water.

10. Composition according to claim 1, wherein the composition is free of silicone compounds and/or free of paraben and/or is free of alkyl parabens.

11. Method for the preparation of compositions according to claim 1 comprising the steps of
  i) preparing a first phase by mixing the active ingredients a), c), a first part of d), as well as e);
  ii) producing a second phase by mixing at least one of the active ingredients mentioned under f) with water;
  iii) preparing a third phase by mixing the active ingredients b) and the remaining part of d);
  iv) homogenising the first and the second phase by stirring;
  v) mixing the composition obtained in step iv) with the third phase;
  vi) optionally, adding perfume, preservative, betaine, urea and/or other substances to the composition obtained in step v); and
  vii) balancing the pH-value; and
  viii) optionally, venting the composition at room temperature.

12. A skin cream comprising the compositions according to claim 1.

13. A skin moisturizer comprising the composition according to claim 1.

14. Cosmetic for the protection of stressed skin comprising a composition according to claim 1.

15. The skin cream according to claim 12, wherein the cream is for the hands and forearms.

16. The skin moisturizer according to claim 13, wherein the moisturizer is a long-lasting skin moisturiser.

17. Composition according to claim 3, wherein the alkyl esters of acrylic acid in the ingredient b) is C10 to C30 alkyl ester of acrylic acid.

18. Composition according to claim 3, wherein the at least one polymer as the ingredient b) is acrylates/C10-30 alkyl acrylate crosspolymer.

19. Composition according to claim 1, wherein the petrochemical waxes are petrolatum, paraffin wax or microcrystalline waxes.

20. Composition according to claim 1, wherein the at least one ester in the ingredient e) is selected from cetyl palmitate, cetyl stearate, myristyl myristate, and mixtures thereof.

* * * * *